United States Patent [19]

Cristol et al.

[11] Patent Number: 4,582,697

[45] Date of Patent: Apr. 15, 1986

[54] PRODUCTION OF ALUMINUM TRIHYDROXIDE HAVING MEDIAN DIAMETER OF 2 TO 100 MICRONS

[75] Inventors: Benoit Cristol; Jacques Mordini, both of Aix-en-Provence, France

[73] Assignee: Aluminum Pechiney, Paris, France

[21] Appl. No.: 624,669

[22] PCT Filed: Oct. 18, 1983

[86] PCT No.: PCT/FR83/00209

§ 371 Date: Jun. 13, 1984

§ 102(e) Date: Jun. 13, 1984

[87] PCT Pub. No.: WO84/01568

PCT Pub. Date: Apr. 26, 1984

[30] Foreign Application Priority Data

Oct. 20, 1982 [FR] France .................................. 82 17954

[51] Int. Cl.$^4$ .............................. C01F 7/02; B01J 1/12
[52] U.S. Cl. .................................... 423/629; 423/127; 23/301; 23/305 R
[58] Field of Search ................... 423/127, 629; 23/301, 23/305

[56] References Cited

U.S. PATENT DOCUMENTS

| | | | |
|---|---|---|---|
| 3,545,923 | 12/1970 | Mercier et al. | 423/127 |
| 3,649,184 | 3/1972 | Featherston | 423/629 |
| 3,838,980 | 10/1974 | Gnyra | 423/119 |
| 4,234,559 | 11/1980 | Tschamper | 423/127 |
| 4,364,919 | 12/1982 | Yamada et al. | 423/629 |

Primary Examiner—John Doll
Assistant Examiner—Jackson Leeds
Attorney, Agent, or Firm—McDougall, Hersh & Scott

[57] ABSTRACT

A process for the production of aluminum trihydroxide having controlled median diameter of 2 to 100 microns, with a unimodal distribution and minimum deviation, by decomposing a hot supersaturated sodium aluminate solution in the presence of seed aluminum trihydroxide, separating the resultant solid and liquid phases and recovering the solid phase constituted by precipitated aluminum trihydroxide. The process comprises grinding aluminum trihydroxide until the aluminum trihydroxide has a specific BET surface area of at least 1 m$^2$/g, introducing the ground aluminum trihydroxide into a hot fraction of the supersaturated sodium aluminate solution to precipitate trihydroxide seed and then decomposing the remaining fraction of the supersaturated sodium alimuniate solution in the presence of the seed. This decomposition leads to the precipitation of aluminum trihydroxide having the required median diameter.

19 Claims, No Drawings

PRODUCTION OF ALUMINUM TRIHYDROXIDE HAVING MEDIAN DIAMETER OF 2 TO 100 MICRONS

This invention relates to a process for the production of aluminium trihydroxide having a median diameter which can be varied within the range of 2 to 100 microns, having a unimodal distribution and minimum deviation. The aluminium trihydroxide is produced by the decomposition of a hot supersaturated solution of sodium aluminate in the presence of an auxiliary seed which has itself been obtained by the decomposition of a supersaturated solution of sodium aluminate in the presence of ground aluminium trihydroxide having a specific surface area, measured according to the B.E.T. method, of at least one square meter per gram.

It is well established in the art to carry out the precipitation of aluminium trihydroxide from a supersaturated solution of sodium aluminate by the addition of a primer consisting of previously crystallised aluminium trihydroxide. The spontaneous generation of seed crystals in a solution of this type has been found to be extremely slow and difficult to produce and even non-existent, depending on the conditions of temperature and concentration of the treated medium.

For this reason, it is common practice in the Bayer process to favour the precipitation of the aluminium trihydroxide from supersaturated sodium aluminate solutions resulting from the alkaline attack of aluminous ores due to the recycling of a considerable fraction of the aluminium trihydroxide which is obtained in a previous cycle.

However, such as it is carried out, this priming process results not only in the recycling of a very considerable quantity of previously precipitated aluminium trihydroxide but above all in grains of aluminium trihydroxide of eminently variable size. The median dimensions and the deviation about this value are difficult to control due to the fact that the dimensions of the grains of aluminium trihydroxide increase during the consecutive cycles and cause the formation of new seeds in a periodic rhythm.

However, those skilled in the art would like to be able to produce, for particular uses, aluminium trihydroxide, the median diameter of the precipitated particle size of which is controlled, i.e. whose granulometry deviates only slightly about the median size.

In fact, certain uses of aluminium trihydroxide require a granulometry which is specific to them. In particular for uses such as, fireproofing charges for synthetic polymers, gentle abrasives in cosmetology, and catalytic substrates.

By the number of publications issued in this field, the specialist literature reveals the importance and the complexity of the research carried out by those skilled in the art to try to provide industrially viable solutions to the above-mentioned problems and to control the size of the aluminium trihydroxide particles.

Among the numerous solutions which have been proposed, some lead to the use of mechanical means and others, which are more numerous, lead to processes which use the resources of chemistry.

The first group which uses mechanical means concerns the production of aluminium trihydroxide, the median diameter of which is generally between 6 and 30 microns, by grinding a coarse aluminium trihydroxide which is obtained by the Bayer process. Such a process is described in French Pat. No. 2 298 510 which claims the production of an aluminium hydroxide intended for use in cosmetology, of which the mean diameter is less than 25 microns, by grinding a coarse hydroxide in the presence of an organic acid. Such a process can be used in the production of an aluminium hydroxide having a mean diameter greater than 15 microns, because it remains reasonable in terms of energy consumption and technological investment. However, if an aluminium hydroxide is to be produced which has a much smaller mean diameter, such as between 15 and 1 microns, the use of such a means is extremely costly because the mean diameter which is required demands a considerable energy consumption and the use of a very high grinding capacity.

The second group which uses chemical resources proposes processes for producing an aluminium trihydroxide having a regulated granulometry and comprises carrying out the decomposition of supersaturated sodium aluminate solutions in the presence of very fine aluminium trihydroxide acting as a primer, the particle size of which will increase during the various stages of precipitation.

A first process which has several stages, described in French Pat. No. 1 290 582, initially comprises preparing the priming material consisting of aluminium trihydroxide having very fine and regular grains, then using this priming material for the decompositions in successive steps, of a supersaturated solution of sodium aluminate. The priming material is prepared by the sudden and violent dilution of a strongly concentrated sodium aluminate solution, having a molecular ratio of $Na_2O/Al_2O_3$ as close as possible to unity, thus causing marked supersaturation of the aluminium trihydroxide which separates in the form of a gel. This gel is formed from spherules swollen with water, containing numerous microscopic seeds of aluminium hydroxide having a mean diameter of between 0.3 and 0.5 microns.

When the primary material having very small grains has been prepared, it is presented as an aqueous suspension in its mother solution, into which the supersaturated aqueous solution of sodium aluminate to be decomposed is introduced in stages; each introduction stage being followed by several hours of agitation. This agitation is continued after the final introduction of the solution to be decomposed until decomposition is complete.

Another process described in French Pat. No. 1 525 133 involves firstly preparing a very fine and very active primary initiator of aluminium trihydroxide by decomposing a dilute solution of sodium aluminate in the presence of a small quantity of an alumina gel which was prepared by the neutralisation of a sodium aluminate solution using a mineral acid. This primary initiator is then used to decompose a supersaturated solution of sodium aluminate. The precipitated aluminium trihydroxide is separated and used as an initiator for decomposing another supersaturated sodium aluminate solution and the process is repeated until the particles of precipitated aluminium trihydroxide have reached the desired size.

French Pat. No. 2 041 750 discloses a process which involves firstly producing a very fine initiator by carbonation of a sodium aluminate solution at a controlled temperature until it is completely neutralised, thus producing an alumina gel. The alumina gel is transformed into a stable crystalline phase by suspending it in a supersaturated sodium aluminate solution. The suspension is stirred for a sufficient length of time and then the initiator is used to prepare an aluminium trihydroxide of the desired granulometry by the decomposition of a supersaturated sodium aluminate solution.

Thus, from the various known publications employing chemical resources, it appears that the processes proposed for attempting to produce an aluminium trihydroxide of regulated granulometry by precipitation from a hot, supersaturated solution of sodium aluminate involve the preparation of an alumina gel and its transformation into a stable crystalline phase whose aluminium hydroxide particle size will increase during the various stages of precipitation. However, the skilled man must note that the processes proposed provide incomplete and unsatisfactory solutions as they lead to the production of aluminium trihydroxide whose size is inadequately controlled due to the poor reproducibillity of the gel quality and the poor stability of the gel in the time.

For this reason, based on the above-mentioned disadvantages, in continuing our research, we have found and perfected a process for the production of aluminium trihydroxide having a median diameter which can be varied within the range of 2 to 100 microns by decomposition of a hot supersaturated sodium aluminate solution in the presence of an initiator. This process is free from the above-mentioned disadvantages.

Accordingly, the present invention provides for the production of aluminium trihydroxide having a median diameter which can be varied as required within the range of 2 to 100 microns and is characterised in that, in a first stage, aluminium trihydroxide is subjected to grinding until a ground aluminium hydroxide is produced which has a specific BET surface area, formed by the grinding operation, of at least 1 m$^2$/g, said ground aluminium trihydroxide is then introduced into a hot fraction of a supersaturated sodium aluminate solution in a sufficient quantity for the total surface of the ground aluminium trihydroxide introduced to be at least 10 square meters per liter of the said fraction, and the suspension thus formed is stirred for a period leading to the precipitation of at least 10% by weight of the alumina present in the supersaturated sodium aluminate solution in the form of aluminium trihydroxide particles constituting an auxiliary seed and, in a second stage, the remaining fraction of the supersaturated sodium aluminate solution is decomposed in the presence of the auxiliary seed, this decomposition leading to the precipitation of aluminium trihydroxide having the desired median diameter by stirring of the suspension formed until a ratio by weight of dissolved $Al_2O_3$ to caustic $Na_2O$ of at most 0.8 is obtained.

To facilitate the subsequent description of the invention, it should be noted that the concentration of caustic $Na_2O$ in grams per liter of the sodium aluminate solution expresses, as is well known, the total quantity of $Na_2O$ present in the said solution in the bonded form of sodium aluminate and in the free form of sodium hydroxide.

During our research, and in an attempt to improve the processes proposed by the prior art recommending the use of alumina gel, we attempted to substitute previously ground aluminium trihydroxide for said gel. We then observed with great interest that the introduction of this ground aluminium trihydroxide into a supersaturated solution of sodium aluminate caused precipitation of an aluminium trihydroxide, the median diameter of which was clearly smaller than the median diameter of the ground aluminium trihydroxide which we had introduced, whereas according to our knowledge of the prior art we were expecting an increase in the median diameter. From then on, continuing further in our research we wished to verify the extent of this observation and, in order to do this, in new experiments, we substituted for the ground aluminium trihydroxide a precipitated aluminium trihydroxide having the same median diameter and an almost identical distribution. We then found that, in the latter case, the median diameter of the precipitated aluminium trihydroxide increased significantly as in the process of the prior art.

Thus, we were able to state that the use of ground aluminium trihydroxide in the decomposition of a supersaturated solution of sodium aluminate resulted in a very different behaviour compared to that of unground aluminium trihydroxide of the same granulometry.

In furthering our research, we used as auxiliary seed the product precipitated during the decomposition of a sodium aluminate solution in the presence of ground aluminium trihydroxide and found that we could obtain an aluminium trihydroxide precipitate of regulated granulometry by decomposing a sodium aluminate solution in the present of said auxiliary seed.

In order to gain a better comprehension of the parameters playing a part in the present process, we completed our research with the objective of controlling the conditions which are most favourable for the production of an aluminium trihydroxide having a granulometry which can be varied as required.

The specific BET surface area developed by the grinding operation is given by the difference between the specific surface area of the ground aluminium trihydroxide and the specific surface area of the aluminium trihydroxide before it is subjected to the grinding operation. As already stated, the specific BET surface area which results during the grinding of aluminium trihydroxide must be at least 1 square meter per gram. It is generally between 2 and 20 m$^2$ per gram and preferably between 3 and 8 m$^2$ per gram.

The grinding operation of the aluminium trihydroxide, which is carried out using any apparatus known to those skilled in the art, may be carried out dry, but it may be desirable to carry out this operation in a liquid medium. In the latter case, the liquid phase which is used to suspend the trihydroxide in an aqueous medium which may be water.

The supersaturated solution of sodium aluminate which is treated according to the process of this invention generally results from the hot alkaline attack of an aluminous ore, such as bauxite, according to the Bayer process widely described in the specialist literature and well known to those skilled in the art. However, this solution can also be of synthetic origin. Whatever its origin, the supersaturated solution of sodium aluminate generally has a concentration of caustic $Na_2O$ of between 50 and 200 grams and preferably between 90 and 170 grams of $Na_2O$ per liter of sodium aluminate solution to be decomposed.

Moreover, it is desirable for this supersaturated solution of sodium aluminate to have a ratio by weight of dissolved $Al_2O_3$ to caustic $Na_2O$ of between 0.8 and 1.3 but preferably between 1.0 and 1.2.

According to the second stage of the process, the fraction of supersaturated sodium aluminate solution in which the crushed aluminium trihydroxide is introduced represents at most 90% by volume and preferably from 5 to 50% by volume of the total quantity of the said solution to be decomposed.

Similarly, the quantity of aluminium trihydroxide crushed by methods known to the skilled man and introduced during the first stage into the fraction of supersaturated sodium aluminate solution to be decomposed is such that the total surface area of the crushed aluminium trihydroxide introduced into the said solution is between 20 and 400 m² per liter and preferably between 40 and 150 m² per liter of supersaturated sodium aluminate solution.

As the crushed aluminium trihydroxide is introduced in a sufficient quantity into the hot fraction of the supersaturated sodium aluminate solution, the suspension thus created is stirred and kept in this state until generally 15 to 75% by weight and preferably 40 to 60% by weight of the alumina present in the supersaturated sodium aluminate solution precipitates in the form of aluminium trihydroxide particles constituting the auxiliary seed.

The aqueous suspension of the auxiliary seed can optionally be subjected to liquid-solid separation during which the solid phase is isolated for use in the second stage of the process.

According to the second stage of the process, the remaining fraction of the supersaturated sodium aluminate solution which has not been subjected to the first stage is decomposed in the presence of the auxiliary seed introduced either in solid form once liquid-solid separation has been carried out at the end of the first stage or in the form of the aqueous suspension of the said auxiliary seed collected before separation is carried out.

This decomposition takes place in a stirred medium and is continued until a ratio by weight of dissolved $Al_2O_3$ to caustic $Na_2O$ generally between 0.75 and 0.40 and preferably between 0.70 and 0.45 is obtained.

During the second stage, the auxiliary seed and the remaining fraction of the supersaturated sodium aluminate solution can be brought together for producing the suspension and permitting its decomposition by introducing:
either all the said remaining fraction at once,
or the portions of the said remaining fraction in at least two stages.

Thus, the decomposition of the remaining fraction of the supersaturated sodium aluminate solution during the second stage of the process according to the invention in the presence of the auxiliary seed originating from the first stage leads, at the end of these two stages, to the precipitation of aluminium trihydroxide having the required median diameter.

The fractions of the supersaturated sodium aluminate solution are decomposed in both stages of the process at a temperature generally between 30° C. and 80° C. but preferably between 45° C. and 65° C.

In practice, the two stages of the process for obtaining aluminium trihydroxide of median diameter which can be varied as required within the range of 2 to 100 microns take place according to the following sequences:
(a) in the first stage:
a-1. Some aluminium trihydroxide is crushed until a crushed aluminium trihydroxide having a specific BET surface area developed by crushing of at least 1 m²/g is obtained.
a-2. The crushed aluminium trihydroxide is introduced into a hot fraction of a supersaturated sodium aluminate solution in a sufficient quantity for the total surface area of the introduced trihydroxide to be at least 10 m²/l of the supersaturated aluminate solution to be decomposed.
a-3. The suspension created in the sequence a-2 is stirred until at least 10% by weight of the alumina present in the aluminate solution precipitates in the form of aluminium trihydroxide constituting the auxiliary seed.
(b) in the second stage:
b-1. The auxiliary seed originating from the sequence a-3 and the remaining fraction of the supersaturated sodium aluminate solution are brought together.
b-2. The remaining fraction of supersaturated sodium aluminate is decomposed by heat in the presence of said seed by stirring the suspension from b-1 and continuing stirring until a ratio by weight of dissolved $Al_2O_3$ to caustic $Na_2O$ of at most 0.8 is obtained. This decomposition causes the precipitation of aluminium trihydroxide having the required median diameter.

The process according to the invention for producing aluminium trihydroxide of a median diameter which can be varied as required is in two stages: One stage involves the preparation of an auxiliary seed and the other the decomposition of a supersaturated sodium aluminate solution in the presence of the seed. These stages can be carried out continuously or intermittently.

The essential features of the invention will be understood better by the following description of examples.

EXAMPLE 1

This example illustrates the possibility according to the invention of producing aluminium trihydroxide particles of median diameter which can be varied as required by using variable quantities of auxiliary seed during the decomposition of the supersaturated sodium aluminate solution.

For this purpose, and in the first stage of the process according to the invention, some industrial aluminium trihydroxide originating from the alkaline attack of a bauxite by the Bayer process has been taken. An aqueous suspension of the said aluminium trihydroxide containing 350 g/l of dry substance was then produced in order to crush it.

Crushing was carried out using an apparatus of known type composed of a cylinder with a horizontal rotational axis and a useful diameter of 100 mm, of which the crushing support is constituted by steel beads. One liter of the above-mentioned suspension was thus crushed using 2 kg of beads having a diameter of 9 mm and 1 kg of beads having a diameter of 6 mm.

After a crushing time of 10 hours, crushed aluminium trihydroxide particles having a BET surface area of 8.6 m²/g measured by the method described in the AFNOR standards NF X 11-621 and X 11-622 were obtained, whereas the aluminium trihydroxide had a BET surface area before crushing of 0.10 m²/g.

Subsequently, and for preparing the auxiliary seed, a supersaturated sodium aluminate solution originating from the Bayer process, which had the following composition in grams per liter was used:
$Al_2O_3$: 176 g/l
Caustic $Na_2O$: 160 g/l
Ratio $Al_2O_3$/caustic $Na_2O$: 1.1
Carbonated $Na_2O$: 14 g/l
Organic C: 7 g/l Cl: 9 g/l Three liters of the said solution was then introduced into a suitable reactor and 45 g of crushed aluminium trihydroxide (in the form of a suspension in water) so as to provide 15 g of crushed aluminium trihydroxide per liter of supersaturated sodium aluminate solution to be decomposed. The suspension thus produced was stirred using a vertical axis stirrer with large blades turning at 60 rpm. The temperature of the suspension was maintained at 60° C. throughout the decomposition operation which lasted 48 hours.

At the end of decomposition, the ratio by weight of dissolved $Al_2O_3$/caustic $Na_2O$ was 0.6, indicating that 45% of the alumina in solution had precipitated.

The aluminium trihydroxide collected at the end of this first stage then washed and dried constituted the auxiliary seed used in the second stage of the process, and had a median diameter of 1.8 microns which was measured by the so-called "laser granulometry" method using a CILAS 715 apparatus.

In the second stage of the process according to the invention, the above-mentioned sodium aluminate solution originating from the Bayer process was decomposed in the presence of the above-mentioned auxiliary seed using the same apparatus and adopting the same experimental conditions for the speed of stirring, temperature and time as in the first stage of the process.

Five decomposition tests, each carried out on 2 liters of the supersaturated sodium aluminate solution, were carried out in the presence of the auxiliary seed introduced in an increasing quantity.

At the end of decomposition, the aluminium trihydroxide collected for each test was washed, dried and the median diameter determined by the "laser granulometry" method.

All the results have been compiled in Table 1 below.

TABLE I

| QUANTITY OF AUXILIARY SEED IN g/l OF SOLUTION TO BE DECOMPOSED | MEDIAN DIAMETER OF THE ALUMINIUM TRIHYDROXIDE PRODUCED |
| --- | --- |
| Test 1 | 5 | 38.0 |
| Test 2 | 15 | 12.2 |
| Test 3 | 25 | 7.5 |
| Test 4 | 35 | 5.0 |
| Test 5 | 55 | 4.0 |

The median diameter of the aluminium trihydroxide collected at the end of the two stages of the process therefore depends on the quantity of auxiliary seed used during the second stage of decomposition.

EXAMPLE 2

This example illustrates the possibility of producing aluminium trihydroxide of large median diameter (bulk product) as required by the process of the invention.

In the first stage of the process according to the invention, some industrial aluminium trihydroxide originating from the alkaline attack of a bauxite by the Bayer process was used. An aqueous suspension of the said aluminium trihydroxide containing 350 g/l of dry substance was produced in order to crush it.

Crushing was carried out in the same apparatus and by the same method as in example 1. One liter of the above-mentioned suspension was thus crushed using 2 kg of beads having a diameter of 9 mm and 1 kg of beads having a diameter of 6 mm. After a crushing time of one hour 30 minutes, crushed aluminium trihydroxide particles having a BET surface area of 2.6 $m^2/g$ were obtained whereas the aluminium trihydroxide had a BET surface area of 0.1 $m^2/g$ before crushing.

Subsequently, and for preparing the auxiliary seed, a supersaturated sodium aluminate solution originating from the Bayer process and having the same composition as in example 1 was used. Two liters of the said solution were then introduced into a suitable reactor and 30 g of the crushed aluminium trihydroxide (in the form of a suspension in water) was introduced so as to provide 15 g of crushed aluminium trihydroxide per liter of supersaturated sodium aluminate solution to be decomposed. The suspension thus produced was stirred using a vertical axis stirrer with wide blades rotating at 60 rpm. The temperature of the suspension was maintained at 60° throughout the decomposition operation which lasted 48 hours.

At the end of decomposition, the ratio by weight of dissolved $Al_2O_3$/caustic $Na_2O$ was 0.65, thus indicating that 41% of the alumina in solution had precipitated.

The aluminium trihydroxide collected, constituting the auxiliary seed used in the second stage, had a median diameter of 3.9 microns.

In the second stage of the process according to the invention, a sodium aluminate solution of the same origin and the same composition as in example 1 was decomposed in the presence of the auxiliary seed originating from the first stage and used in a proportion of 5 g/l of the said solution.

The decomposition effected on a volume of 2 liters of the said solution was carried out in the same apparatus under the same experimental conditions of stirring speed, temperature and time as in the first stage of the process.

At the end of this second stage, the ratio between the mass of aluminium trihydroxide collected, washed and dried and the mass of crushed aluminium trihydroxide used in the first stage of the process was 170.

Moreover, the aluminium trihydroxide collected at the end of the said second stage had its median diameter determined by the "laser granulometry" method which had also been applied to the crushed aluminium trihydroxide and the auxiliary seed collected at the end of the first stage, with the aim of carrying out comparative analysis of the results.

The results of granulometric analysis of the aluminium trihydroxide after crushing, after the first decomposition (auxiliary seed) and after the second decomposition were combined in Table II below:

TABLE II

| DIAMETER IN MICRONS | CRUSHED Al TRIHYDROXIDE: PERCENTAGE SMALLER THAN: | AUXILIARY SEED: PERCENTAGE SMALLER THAN: | Al TRIHYDROXIDE PRODUCED: PERCENTAGE SMALLER THAN |
| --- | --- | --- | --- |
| 1 | 4.4 | 11.5 | 1.3 |
| 2 | 10.6 | 27.6 | 1.9 |
| 3 | 16.7 | 42.3 | 2.3 |
| 4 | 22.8 | 52.2 | 3.0 |
| 6 | 33.5 | 59.9 | 4.2 |
| 8 | 43.3 | 63.5 | 5.6 |
| 12 | 61.0 | 71.3 | 7.9 |
| 16 | 73.0 | 78.7 | 8.9 |
| 24 | 85.0 | 87.6 | 9.0 |
| 32 | 91.0 | 92.5 | 14.0 |
| 48 | 96.0 | 95.7 | 38.0 |

TABLE II-continued

| DIAMETER IN MICRONS | CRUSHED Al TRIHYDROXIDE: PERCENTAGE SMALLER THAN: | AUXILIARY SEED: PERCENTAGE SMALLER THAN: | Al TRIHYDROXIDE PRODUCED: PERCENTAGE SMALLER THAN |
|---|---|---|---|
| 64 | 98.0 | 98.0 | 57.0 |
| 96 | 100.0 | 100.0 | 75.0 |
| 128 | 100.0 | 100.0 | 90.0 |
| MEDIAN DIAMETER $d_{50}$ IN MICRONS | 10 | 3.9 | 58 |

This table therefore shows than the median diameter of the auxiliary seed used in the second stage is smaller than the median diameter of the crushed product for obtaining the auxiliary seed. Moreover, this Table shows that it is possible to obtain a large diameter aluminium trihydroxide at will.

EXAMPLE 3

This example illustrates the possibility of producing aluminium trihydroxide with a small median diameter at will by the process according to the invention.

In the first stage of the process according to the invention, some industrial aluminium trihydroxide originating from the Bayer process was used. An aqueous suspension of the said aluminium trihydroxide containing 350 g/l of dry substance was then produced in order to crush it.

Crushing was carried out using the same apparatus and according to the same set values as in example 1. After a crushing time of three hours, crushed particles of aluminium trihydroxide having a BET surface area of 4 $m^2/g$ were obtained whereas the aluminium trihydroxide intended for this crushing had a BET surface area of 0.1 $m^2/g$.

Subsequently, and for preparing the auxiliary seed, a supersaturated sodium aluminate solution originating from the Bayer process, which had the same composition as the one quoted in example 1 was used. Two liters of the said solution and 36 g of the crushed aluminium trihydroxide (in the form of a suspension in water) was then introduced so as to provide 18 g of crushed aluminium trihydroxide per liter of supersaturated sodium aluminate solution to be decomposed. The suspension produced in this way was stirred using a vertical axis stirrer with wide blades rotating at 60 rpm. The temperature of the suspension was kept at 60° C. throughout the decomposition operation which lasted 48 hours.

At the end of decomposition, the ratio by weight of dissolved $Al_2O_3$ to caustic $Na_2O$ was 0.62, thus indicating that 43% of the alumina in solution had precipitated. The aluminium trihydroxide produced constituted the auxiliary seed used in the second stage of the process. It had a median diameter of 1.9 microns.

In the second stage of the process according to the invention, a sodium aluminate solution of the same origin and the same composition as in example 1 was decomposed in the presence of 70 g of auxiliary seed per liter of supersaturated sodium aluminate solution to be decomposed.

For this purpose, 2 liters of the supersaturated sodium aluminate solution described in example 1 of which the temperature was 50° C. were added to 52% by volume of the suspension of auxiliary seed originating from the first stage. Decomposition was carried out in the same apparatus and adopting the same other experimental conditions for stirring speed and time as in the first stage of the process.

At the end of this second stage, the ratio between the mass of aluminium trihydroxide collected, washed and dried and the mass of aluminium trihydroxide crushed and used in the first stage 25. Moreover, the aluminium trihydroxide collected at the end of the said second stage had its median diameter determined by the "laser granulometry" method which was also applied to the crushed aluminium trihydroxide and to the auxiliary seed collected at the end of the first stage with the aim of carrying out comparative analysis of the results.

The results of granulometric analysis of the aluminium trihydroxide taken after crushing, after first decomposition (auxiliary seed) and after second decomposition were combined in Table III below:

TABLE III

| DIAMETER IN MICRONS | CRUSHED Al TRIHYDROXIDE: PERCENTAGE SMALLER THAN: | AUXILIARY SEED: PERCENTAGE SMALLER THAN: | Al TRIHYDROXIDE PRODUCED: PERCENTAGE SMALLER THAN |
|---|---|---|---|
| 1 | 5.9 | 23.5 | 10.9 |
| 2 | 14.8 | 52.3 | 20.7 |
| 3 | 24.5 | 68.0 | 33.4 |
| 4 | 33.7 | 76.5 | 49.9 |
| 6 | 49.3 | 83.1 | 76.8 |
| 8 | 61.4 | 86.9 | 90.0 |
| 12 | 79.2 | 92.6 | 97.9 |
| 16 | 89.2 | 95.6 | 100 |
| 24 | 95.9 | 96.8 | 100 |
| 32 | 98.3 | 97.0 | 100 |
| 48 | 99.7 | 97.6 | 100 |
| 64 | 100 | 98.0 | 100 |
| 96 | 100 | 100 | 100 |
| 128 | 100 | 100 | 100 |
| MEDIAN DIAMETER $d_{50}$ IN MICRONS | 6.1 | 1.9 | 4 |

This Table therefore shows the development of the median diameter of the crushed aluminium trihydroxide, the auxiliary seed obtained and the aluminium trihydroxide produced at the end of the second stage of the process.

Moreover, this Table confirms the production on demand of a final product of small median diameter, by using a large quantity of auxiliary seed in the second stage of the process.

EXAMPLE 4

This example illustrates the possibility of producing aluminum trihydroxide on demand, the particles of which have not only a regulated median diameter but also the particle diameters deviate minimally.

In the first stage of the process according to the invention, industrial aluminium trihydroxide originating from the Bayer process was used. Then, for the purpose of crushing, an aqueous suspension of the said aluminium trihydrate containing 350 g/l of dry substance was produced. Crushing was carried out using the same apparatus as in the preceding examples and by the same method. After a crushing time of 3 hours, crushed aluminium trihydroxide particles having a BET surface area of 4 m²/g was obtained, whereas the aluminium trihydroxide had a BET surface area before crushing of 0.10 m²/g.

Subsequently, and for preparing the auxiliary seed, a supersaturated sodium aluminate solution originating from the Bayer process, which had the same composition as the one quoted in example 1, was used. The charge of crushed aluminium trihydroxide which was introduced into the sodium aluminate solution was 15 g/l, the conditions of temperature (60° C.) and time (48 hours) were the same as in Example 1.

At the end of decomposition, the ratio by weight of dissolved $Al_2O_3$ to caustic $Na_2O$ was 0.62 thus indicating that 43% of the alumina in solution had precipitated. The aluminium trihydroxide produced constituted the auxiliary seed used in the second stage of the process. It had a median diameter of 2 microns.

In the second stage of the process according to the invention, a solution of sodium aluminate of the same origin and the same composition as in example 1 was decomposed in the presence of the auxiliary seed with stirring. For this purpose, a quantity of the supersaturated sodium aluminium solution described in example 1, equal to 18 times the volume of the suspension of the said seed was added to the suspension of auxiliary seed originating from the first stage, this addition being effected in three periods of 24 hours respectively. The quantity of the said solution added during each period represents 15%, 30% and 55% by volume of the total quantity of supersaturated aluminate solution to be introduced.

Decomposition was carried out in a homothetic apparatus 15 times larger than the apparatus used in the first stage and by adopting the same other experimental conditions of temperature and time as in the first stage of the process.

At the end of this second stage, the aluminium trihydroxide collected had its median diameter determined by the "laser granulometry" method, of which the results are compiled in Table IV below at the same time as those relating to a product of the same median diameter obtained during the second decomposition by the addition in a single dose of the supersaturated sodium aluminate solution to the suspension of the auxiliary seed.

TABLE IV

| | PERCENTAGE SMALLER THAN | |
|---|---|---|
| DIAMETER IN MICRONS | Al TRIHYDROXIDE PRODUCED BY ADDITION IN 3 DOSES OF THE SODIUM ALUMINATE SOLUTION | Al TRIHYDROXIDE PRODUCED BY ADDITION IN 1 DOSE OF THE SODIUM ALUMINATE SOLUTION |
| 1 | 3.2 | 3.2 |
| 2 | 3.2 | 4.4 |
| 3 | 3.2 | 5.0 |
| 4 | 3.7 | 6.1 |
| 6 | 4.7 | 7.3 |
| 8 | 4.8 | 8.5 |
| 12 | 7.1 | 16.9 |
| 16 | 18.3 | 29.6 |
| 24 | 54.1 | 57.3 |
| 32 | 82.9 | 77.5 |
| 48 | 100 | 90.5 |
| 64 | 100 | 93.5 |
| MEDIAN DIAMETER $d_{50}$ IN MICRONS | 23 | 21.6 |
| DEVIATION: | 0.5 | 0.76 |

TABLE IV-continued

| | PERCENTAGE SMALLER THAN | |
|---|---|---|
| DIAMETER IN MICRONS | Al TRIHYDROXIDE PRODUCED BY ADDITION IN 3 DOSES OF THE SODIUM ALUMINATE SOLUTION | Al TRIHYDROXIDE PRODUCED BY ADDITION IN 1 DOSE OF THE SODIUM ALUMINATE SOLUTION |
| $= \dfrac{d_{75} - d_{25}}{d_{50}}$ | | |

This Table therefore shows that a closer granulometry is obtained by adding the sodium aluminate solution in several doses, due in particular to observation of the deviation parameter "e" which is the ratio of the difference between the diameter $d_{75}$ and the diameter $d_{25}$ to the median diameter $d_{50}$.

EXAMPLE 5

This example illustrates the industrial production of aluminium trihydroxide of granulometry which can be varied on demand by carrying out the process in two stages according to the invention, that is to say, by decomposition of a supersaturated sodium aluminate solution in the presence of an auxiliary seed.

In the first stage of the process, an industrial aluminium trihydroxide obtained by the Bayer process and subjected to a crushing operation in a vibrating crusher of a known type (PALLA U 20 of HUMBOLT) treating a volume of suspension corresponding to 22 kilos per hour of dry substance was used. This crushing produced a crushed hydrate having a BET surface area developed by crushing of 4 m²/g.

Subsequently, and for preparing the auxiliary seed, a 160 m³ tank provided with a vertical axis stirrer rotating at a speed of 7 rpm and capable of stirring a suspension occupying a small proportion of the total volume of the said tank was used. Moreover, the super-saturated sodium aluminate solution to be decomposed was taken from the circuit of a Bayer factory, the $Al_2O_3$ concentration being 165 g/l whereas the caustic $Na_2O$ concentration was 150 g/l giving a ratio by weight of dissolved $Al_2O_3$ to caustic $Na_2O$ of 1.1.

33 m³ of the said supersaturated sodium aluminate solution was then introduced into the above-mentioned tank, the temperature of the medium being adjusted to 55° C. 500 kg of crushed aluminium trihydroxide in suspension in 1 m³ of water were then also pumped in, the quantity of crushed aluminium trihydroxide being 15 g/l. After 40 hours at 55° C., the ratio by weight of dissolved $Al_2O_3$ to caustic $Na_2O$ was 0.57. The content of dry substance was 137 g/l of precipitated aluminium trihydroxide and the median diameter of this auxiliary seed was 2.2 microns.

In the second stage of the process according to the invention, 120 m³ of a supersaturated sodium aluminate solution at 60° C. was added to the suspension obtained in the first stage. The medium thus obtained was kept at this temperature with stirring for 40 hours. At the end of this second stage, the ratio by weight of the dissolved $Al_2O_3$ to caustic $Na_2O$ was 0.635.

The granulometry of the final product was as follows:

| MICRON | 1 | 2 | 3 | 4 | 6 | 8 | 12 | 16 |
|---|---|---|---|---|---|---|---|---|
| % PASSING | 10 | 14 | 15 | 22 | 41 | 64 | 90 | 100 |

This granulometry afforded a median diameter of 7.2 microns and a minimal deviation of diameters about this value.

We claim:

1. A process for the production of aluminium trihydroxide having a median diameter of 2 to 100 microns, comprising the steps of in a first stage, grinding aluminum trihydroxide until it has a specific BET suface area of at least 1 $m^2/g$, bringing said ground aluminum trihydroxide into contact with a hot fraction of a supersaturated sodium aluminate solution in a quantity such that the total surface area of the aluminum trihydroxide which is introduced in ground form is at least 10 $m^2/l$ of said fraction, said sodium aluminate solution having a caustic $Na_2O$ concentration of between 50 g/l and 200 g/l, and a rato by weight of dissolved $Al_2O_3$ to caustic $Na_2O$ of between 0.8 and 1.3, and then stirring the resulting suspension at a temperature of from 30° to 80° C. for a period leading to the precipitation of at least 10% by weight of the alumina present in the supersaturated sodium aluminate solution in the form of aluminum trihydroxide particles constituting an auxiliary seed, said auxiliary seed having a median diameter smaller than that of the initial ground aluminum trihydroxide, and, in a second stage, bringing said auxiliary seed into contact with the remaining fraction of the supersaturated sodium aluminate solution to form a suspension, decomposing the sodium aluminate present in the suspension by heating at a temperature of from 30° to 80° C. and by stirring said suspension until a ratio by weight of dissolved $Al_2O_3$ to caustic $Na_2O$ of at most 0.8 is obtained, resulting in the precipitation of aluminum trihydroxide having a median diameter of 2 to 100 microns, then separating the precipitated aluminum trihydroxide product from the decomposed sodium aluminate solution.

2. A process for the production of aluminum trihydroxide according to claim 1, wherein the specific BET surface area developed by crushing is between 2 and 20 $m^2/g$.

3. A process for the production of aluminum trihydroxide according to claim 1, wherein the aluminum trihydroxide is crushed dry.

4. A process for the production of aluminum trihydroxide according to claim 1, wherein the aluminum trihydroxide is crushed in suspension in an aqueous medium.

5. A process for the production of aluminum trihydroxide according to claim 1, wherein the supersaturated, hot solution of sodium aluminate has a caustic $Na_2O$ concentration of between 90 g/l and 170 g/l.

6. A process for the production of aluminum trihydroxide according to claim 1, wherein the supersaturated sodium aluminate solution has a ratio by weight of dissolved $Al_2O_3$ to caustic $Na_2O$ and between 1.0 and 1.2.

7. A process for the production of aluminum trihydroxide according to claim 1, wherein the fraction of the supersaturated sodium aluminate solution used in the first stage represents at most 90% by volume of the total quantity of the said solution to be decomposed.

8. A process for the production of aluminum trihydroxide according to claim 1, wherein the quantity of crushed aluminum trihydroxide used in the first stage for the decomposition of the fraction of supersaturated sodium aluminate solution is such that the total surface area of the crushed aluminum trihydroxide introduced is between 20 and 400 $m^2/l$ of the fraction of the supersaturated sodium aluminate solution to be decomposed.

9. A process for the production of aluminum trihydroxide according to claim 1, wherein the suspension created in the first stage is stirred and kept in this state until 15 to 75% by weight of the alumina present in the supersaturated sodium aluminate solution precipitates in the form of aluminum trihydroxide particles constituting the auxiliary seed.

10. A process for the production of aluminum trihydroxide according to claim 1, wherein the suspension resulting from the first stage is subjected to liquid-solid separation, then the solid phase constituting the auxiliary seed is brought into contact with the remaining fraction of the supersaturated sodium aluminate solution in the second stage.

11. A process for the production of aluminum trihydroxide according to claim 1, wherein the suspension resulting from the first stage is brought into contact with the remaining fraction of the supersaturated sodium aluminate solution in the second stage.

12. A process for the production of aluminum trihydroxide according to claim 1, wherein decomposition of the remaining fraction of supersaturated sodium aluminate solution is continued in the second stage with stirring until a ratio by weight of dissolved $Al_2O_3$ to caustic $Na_2O$ of between 0.75 and 0.40 is obtained.

13. A process for the production of aluminum trihydroxide according to claim 1, wherein the fractions of the supersaturated sodium aluminate solution are decomposed in the two stages at a temperature of between 45° C. and 65° C.

14. A process for the production of aluminum trihydroxide according to claim 1, wherein the auxiliary seed and the remaining fraction of the supersaturated sodium aluminate solution are brought together in the second stage by introducing all the said remaining fraction in one dose.

15. A process for the production of aluminum trihydroxide according to claim 1, wherein the auxiliary seed and the remaining fraction of the supersaturated sodium aluminate solution are brought together in the second stage by introducing all the said remaining fraction in two doses.

16. A process for the production of aluminum trihydroxide according to claim 1, wherein the specific BET surface are developed by crushing is between 3 and 8 $m^2/g$.

17. A process for the production of aluminum trihydroxide according to claim 1, wherein the quantity of crushed aluminum trihydroxide used in the first stage for the decomposition of the fraction of supersaturated sodium aluminate solution is such that the total surface area of the crushed aluminum trihydroxide introduced is between 40 and 150 $m^2/l$ of the fraction of the supersaturated sodium aluminate solution to be decomposed.

18. A process for the production of aluminum trihydroxide according to claim 1, wherein the suspension created in the first stage is stirred and kept in this state until 40 to 60% by weight of the alumina present in the supersaturated sodium aluminate solution precipitates in the form of aluminum trihydroxide particles constituting the auxiliary seed.

19. A process for the production of aluminum trihydroxide according to claim 1, wherein decomposition of the remaining fraction of supersaturated sodium aluminate solution is continued in the second stage with stirring until a ratio by weight of dissolved $Al_2O_3$ to caustic $Na_2 O$ of between 0.70 and 0.45 is obtained.

* * * * *